(12) United States Patent
Della Valle et al.

(10) Patent No.: US 11,744,840 B2
(45) Date of Patent: Sep. 5, 2023

(54) N-PALMITOYL-D-GLUCOSAMINE IN A MICRONIZED FORM

(71) Applicant: Innovet Italia S.R.L., Milan (IT)

(72) Inventors: Francesco Della Valle, Milan (IT); Maria Federica Della Valle, Milan (IT); Gabriele Marcolongo, Milan (IT); Sofia Parrasia, Milan (IT); Salvatore Cuzzocrea, Milan (IT)

(73) Assignee: Innovet Italia S.R.L., Milan (IT)

( * ) Notice: Subject to any disclaimer, the term of this patent is extended or adjusted under 35 U.S.C. 154(b) by 0 days.

(21) Appl. No.: 17/350,259

(22) Filed: Jun. 17, 2021

(65) Prior Publication Data

US 2021/0308160 A1    Oct. 7, 2021

Related U.S. Application Data

(62) Division of application No. 16/359,943, filed on Mar. 20, 2019, now abandoned.

(30) Foreign Application Priority Data

Mar. 26, 2018  (IT) .................. 102018000003912

(51) Int. Cl.
| | |
|---|---|
| *A61K 31/7008* | (2006.01) |
| *A61P 37/00* | (2006.01) |
| *A61K 9/00* | (2006.01) |
| *A61K 9/14* | (2006.01) |
| *A61K 31/12* | (2006.01) |
| *A61K 31/7034* | (2006.01) |
| *C07H 5/06* | (2006.01) |
| *A61P 29/00* | (2006.01) |
| *C07H 13/06* | (2006.01) |

(52) U.S. Cl.
CPC ........ *A61K 31/7008* (2013.01); *A61K 9/0056* (2013.01); *A61K 9/145* (2013.01); *A61K 31/12* (2013.01); *A61K 31/7034* (2013.01); *A61P 29/00* (2018.01); *A61P 37/00* (2018.01); *C07H 5/06* (2013.01); *C07H 13/06* (2013.01); *C07B 2200/13* (2013.01)

(58) Field of Classification Search
CPC . A61K 31/7008; A61K 31/7034; A61K 31/12
See application file for complete search history.

(56) References Cited

U.S. PATENT DOCUMENTS

| | | | | |
|---|---|---|---|---|
| 2005/0239749 | A1* | 10/2005 | Kambayashi | .......... A61Q 19/00 |
| | | | | 424/70.13 |
| 2007/0270496 | A1* | 11/2007 | Della Valle | ............. A61P 37/08 |
| | | | | 514/563 |

OTHER PUBLICATIONS

Masucci (Emulsion stability basics; Jan. 2017; www.processingmagazine.com/mixing-blending-size-reduction/article/15586907/emulsion-stability-basics).*

Pubmed (pubchem.ncbi.nlm.nih.gov/compound/Palmitic-acid; downloaded Dec. 6, 2022).*

* cited by examiner

*Primary Examiner* — Pancham Bakshi
(74) *Attorney, Agent, or Firm* — MacMillan, Sobanski & Todd, LLC

(57) ABSTRACT

The present invention relates to an N-palmitoyl-D-glucosamine-based composition in a micronized form, optionally in combination with Curcumin.

In particular, the present invention relates to N-palmitoyl-D-glucosamine in a micronized or co-micronized form with Curcumin. Such a product can be formulated in human or veterinary pharmaceutical compositions, dietetic products, food supplements, or foods for special medical purposes (FSMP), or in feeds, or nutritional supplements for animals for the treatment of chronic systemic inflammatory diseases, in humans and animals, resulting from dysfunctions of epithelia and synovial membranes.

13 Claims, 6 Drawing Sheets

N-PALMITOYL-D-GLUCOSAMINE IN A MICRONIZED FORM

CROSS-REFERENCE TO RELATED APPLICATIONS

This is a divisional application of U.S. Ser. No. 16/359,943 filed Mar. 20, 2019, which claims priority to IT 102018000003912 filed Mar. 26, 2018 the entire disclosures of which are expressly incorporated herein by reference.

RELATED FIELD OF THE INVENTION

The present invention relates to an N-palmitoyl-D-glucosamine-based composition in a micronized form.

BACKGROUND ART

The tissues lining the free surfaces of the organism—from the outermost to the smallest surfaces of the internal organs—are divided into epithelia and membranes. The latter cover body cavities in communication or not with the outside. Typical examples are intestinal mucosa and synovial membranes, lining the inner surface of the joint capsule, as well as tendons and ligaments contained in the joint cavity.

These are primarily protective tissues, which—depending on the localization—are associated with sliding and lubrication (e.g. in the synovial membranes of mobile joints) or absorption (e.g. in the intestinal mucosa) functions.

When the defensive function is compromised (such as, following mechanical insults or dismicrobism conditions), dysfunctional states are generated, to which the most advanced biomedical research is reserving a particular attention in recent years.

It is very recent the evidence that these dysfunctions have repercussions not only locally, but also at systemic level, initiating a chronic inflammatory response (CSI). CSI has been shown to originate both from alterations of the synovial membrane—in particular during osteoarthritis—and from dysfunctions of different epithelia.

When the cells of the lining tissues undergo different stresses (noxae), they release pro-inflammatory factors which, through a bidirectional cross-talk with the neighboring immune cells, widen the response to different organs, even distant ones. Among the factors primarily involved in the systemic amplification of inflammatory states caused by synovial membranes and epithelial tissues dysfunctions, particular emphasis is given to particular cytokines and to free radicals or Reactive Oxygen Species (ROS).

Both the proteases released by the immunoinflammatory cells and the ROS generated in situ degrade the glycosaminoglycans (GAG) of the extracellular matrix, resulting in the weakening of the structural and functional barrier and in an increased damage.

These recent knowledges determine a completely new way, both in terms of diagnosis and prevention and therapy, to consider the diseases resulting from dysfunctions of epithelial tissues and membranes resulting in the onset of Chronic Systemic Inflammation (CSI).

The most common chronic systemic inflammation caused by dysfunctions of synovial membranes is Osteoarthritis (OA), a very common disease in both humans and pets. Radiological signs indicative of OA are present in 70% of the elderly human population (over 65) and, in the veterinary field, in just under 30% of the feline population; the symptomatic OA, moreover, affects 10% of men and 13% of women over 60 years of age, affecting, in the veterinary field, as many as 20% of dogs over 1 year of age. Originally classified as a degenerative disease and therefore prerogative of the articular cartilage alone, OA is now recognized as an inflammatory disorder, involving not only the cartilage but all the joint tissues, from the synovial membrane to the tendons, muscles, ligaments and subchondral bone.

Instead, in the dermatological field, among the most frequent chronic systemic inflammations caused by epithelium dysfunctions, there are atopic dermatitis and psoriasis.

Atopic dermatitis is a frequent disease both in humans and in pets, with prevalence of about 20% in children and 8-15% in dogs (depending on the breed) and is also frequently found in cats. The chronic systemic inflammation (CSI) of epithelial origin is confirmed by the co-morbidity between atopic dermatitis and inflammatory and/or neuroinflammatory disorders of other organs.

Psoriasis is a chronic inflammatory cutaneous disease affecting between 2 and 4% of the population. Similar to atopic dermatitis, many recent evidences recognize in psoriasis the origin of a CSI state, which is based on the production of inflammatory cytokines by skin and immunoinflammatory cells, with increased systemic levels of interleukins such as IL-17. The extra-cutaneous repercussions of psoriasis on the articular, cardiovascular, renal, hepatic, and metabolic levels are attributed to this cytokine.

Inflammatory bowel disease (IBD) is an epidemiologically increasing disorder in humans, and frequently found also in dogs and cats. IBD is considered a chronic systemic inflammation disease: the co-morbidity between IBD and orthopedic diseases is an important confirmation of the chronic systemic inflammatory aspect.

Similar observations have been made for disorders of other lining epithelia, and in particular of the bladder urothelium. Patients suffering from interstitial cystitis and recurrent cystitis often complain of concomitant vulvodynia, fibromyalgia, gastroesophageal reflux. Interstitial cystitis and recurrent cystitis, painful disorders present in both the human and feline populations, are in fact characterized by the alteration of the bladder urothelium architecture associated with a high degree of tissue inflammation with increased systemic (serum) inflammatory markers levels and with activation of immune cells.

N-palmitoyl-D-glucosamine (PGA) has been described in the International Publication WO 96/18600 within a class of molecules having activity in diseases connected to an abnormal modulation of the peripheral cannabinoid receptor CB2. Among the potentially treated diseases, chronic or acute joint inflammations such as rheumatoid arthritis are described. However, no experimental data have been reported for this molecule, nor has an effect on chronic systemic inflammatory diseases such as osteoarthritis, psoriasis, atopic dermatitis, intestinal epithelial or bladder diseases been indicated.

Further, WO 96/18600 does not describe N-Palmitoyl-D-Glucosamine in a micronized form.

SUMMARY OF THE INVENTION

The present invention relates to N-palmitoyl-D-glucosamine in a micronized form.

The present invention also relates to a composition of N-palmitoyl-D-glucosamine and Curcumin in a co-micronized form.

The present invention further relates to N-palmitoyl-D-glucosamine in a micronized form, or co-micronized with Curcumin, or co-micronized with Polydatin, for use in the treatment of chronic systemic inflammatory diseases, preferably selected from osteoarthritis, psoriasis, atopic dermatitis, and intestinal epithelial or bladder diseases.

Moreover, the present invention also relates to pharmaceutical formulations, for human or veterinary use, dietary or supplements, or feed, or nutritional supplements for animals, comprising N-palmitoyl-D-glucosamine in a micronized form or co-micronized with Curcumin or polydatin.

The invention also relates to a micronization or co-micronization process specifically designed for the production of N-palmitoyl-D-glucosamine in a micronized form or co-micronized with Curcumin or with polydatin.

These and further objects, as outlined in the appended claims, will be described in the following description. The claim wording must be considered included in the description for the purpose of the evaluation of sufficiency of description.

Further features and advantages of the invention will become apparent from the following description of preferred embodiments, given by way of non-limiting example.

DETAILED DESCRIPTION OF THE INVENTION

In a first aspect, the present invention relates to the N-palmitoyl-D-glucosamine compound (hereinafter also referred to as PGA) in a micronized form.

The general term "compound in a micronized form" refers to a compound having a particle size distribution, defined as a percentage by volume and measured by the laser light scattering method, represented by a distribution curve having the mode below 10 microns but above 0.6 microns.

In one embodiment, PGA has a particle size distribution as defined above, measured with a Malvern Mastersizer 3000 tool with Mie calculation algorithm, where at least 96% by volume of particles have a particle size from 0.6 to 10 microns.

Figure 1:
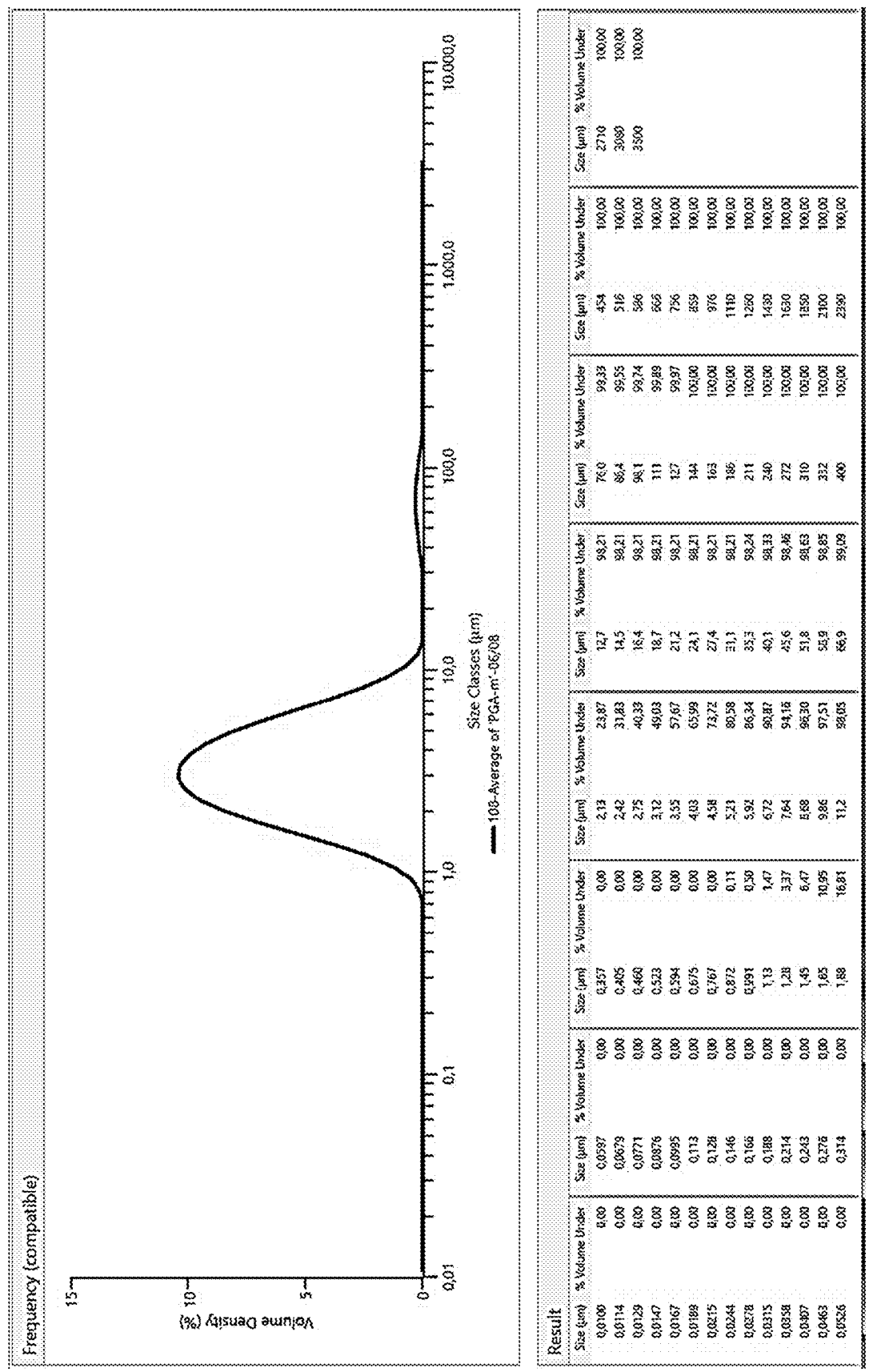
FIG. 1 shows a particle size distribution curve V %/size of N-palmitoyl-D-glucosamine in a micronized form.

In a preferred embodiment, PGA has a particle size distribution as defined above, measured with a Malvern Mastersizer 3000 tool with Mie calculation algorithm, having a mode between 3.1 and 3.5 microns and having at least 97% by volume of particles smaller than 10 microns and preferably at least 50% by volume of particles smaller than 3.5 microns. An example of this particle size distribution is shown in the graph and in the attached table in FIG. 1.

The micronization can be carried out in a fluid jet system (e.g., a Jetmill® model) operating with a compressed air jet "spiral technology" capable of exploiting kinetic energy—instead of mechanical energy—to crush the N-palmitoyl-D-glucosamine particles. These devices are conventional and will therefore not be further described.

Figure 6:
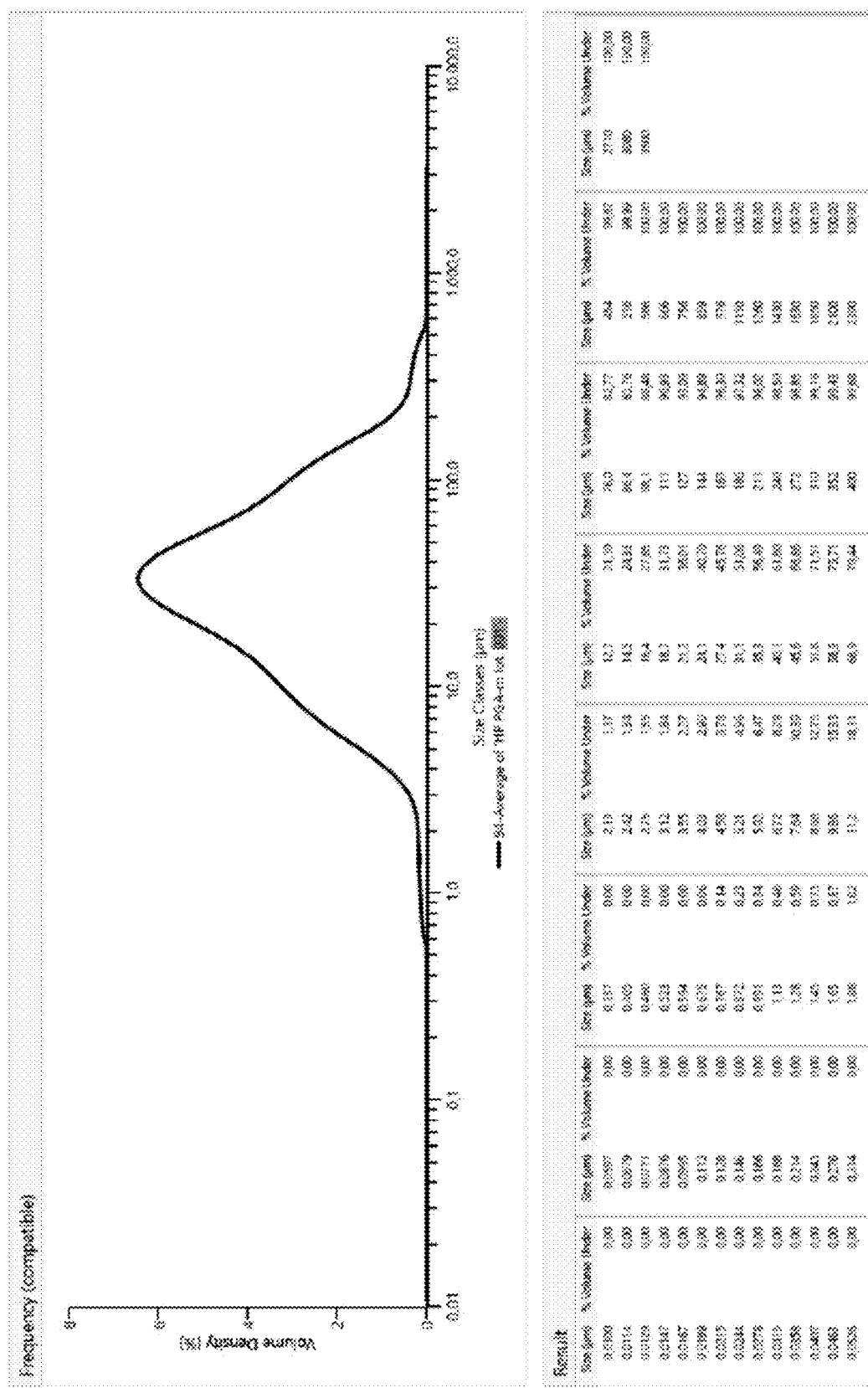
FIG. 6 shows a particle size distribution curve V %/size of N-palmitoyl-D-glucosamine in a non-micronized form.

However, it has been found that by performing the micronization of PGA as such, it is not possible to obtain a particle size distribution compatible with a micronized product as defined above. In fact, a product characterized by an irregular Gaussian curve is obtained with a mode clearly superior to 10 microns, in particular between 31 and 40 microns, as shown in the particle size distribution curve in FIG. 6.

However, it has been surprisingly found that, by previously crystallizing PGA in the presence of a fatty acid and then subjecting the crystallized product to a conventional micronization process—for example with a fluid jet system operating with a compressed air jet spiral technology—PGA can be obtained in a micronized form with the particle size distributions described above.

Preferably, the fatty acid is palmitic acid.

In preferred embodiments, the fatty acid is present in a percentage by weight from 3% to 20%, or from 4% to 15%, or from 4.5% to 6%, with respect to PGA, determined on the finished product by a reverse phase HPLC method, against a reference solution containing authentic palmitic acid.

The PGA crystallization in the presence of the fatty acid includes a step of intimately mixing PGA with the fatty acid, where the latter is in percentages by weight from 2% to 20%, preferably from 4% to 10%, with respect to PGA.

In preferred embodiments, the crystallization process includes the following steps:

a) providing PGA, preferably with a purity >98%, determined by TLC analysis;

b) suspending PGA in a polar solvent along with the fatty acid or a salt thereof, where the fatty acid or a salt thereof is present in amounts by weight from 2% to 20%, or from 4% to 10% with respect to PGA;

c) heating the suspension from step b) at a temperature from 50° C. to 90° C., or at reflux of the solvent, for a time longer than 15 minutes, or longer than 30 minutes, or longer than 1 hour;

d) slowly bringing the crystallization mixture to a temperature below 10° C.;

e) recovering the crystallisate in the form of an intimate mixture of PGA and fatty acid.

As said, the fatty acid is preferably palmitic acid.

The polar solvent is preferably selected from methanol, ethanol, acetone, or ethyl acetate.

Step d) is preferably carried out over 20 minutes, more preferably over 30 minutes.

The synthesis and crystallization of PGA in the presence of a fatty acid are described in detail in the following experimental part.

It has also been found that micronized PGA as described and defined above can be used for the treatment of chronic systemic inflammatory diseases, of humans and animals, resulting from dysfunctions of epithelia and synovial membranes.

In particular, these diseases are preferably selected from:
inflammatory diseases resulting from dysfunctions of the synovial membranes;
inflammatory diseases resulting from dysfunctions of the intestinal mucous membranes;
inflammatory diseases resulting from dysfunctions of the urothelial mucosa;
inflammatory diseases resulting from dysfunctions of the keratinized epithelia.

Therefore, the invention further relates to PGA in a micronized form, preferably PGA in a micronized form comprising from 3% to 20% by weight of a fatty acid, for use in the treatment of inflammatory diseases, preferably chronic systemic inflammatory diseases, of humans and animals, resulting from dysfunctions of epithelia and/or synovial membranes.

It has also been surprisingly found that the association of PGA with Curcumin or Polydatin has an apparent synergistic effect in treating inflammatory diseases.

Curcumin is a molecule extracted from *Curcuma longa* mainly used as a vegetable dye, due to its yellow color. Curcumin has the following chemical structure:

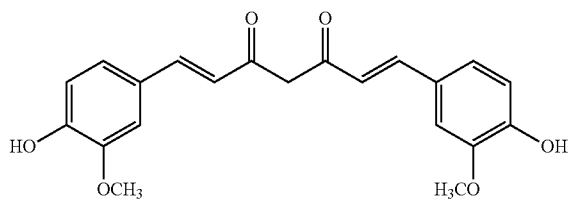 [SMILES: COc1cc(/C=C/C(=O)CC(=O)/C=C/c2ccc(O)c(OC)c2)ccc1O]

Curcumin is a commercial product, for example with a titer of about 95% of total curcuminoids, containing from 60 to 75% of Curcumin as such, from 15 to 25% of desmethoxy-curcumin, and from 2 to 5% of bis-desmethoxy-curcumin.

Polydatin or Piceid is a stilbenoid glucoside derived from resveratrol and present in grape juice. It can also be isolated from the *Polygonum cuspidatum* plant. Its structural formula is

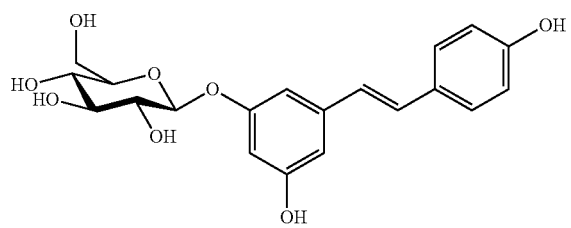

Polydatin is more stable and bioavailable than resveratrol, as it is more resistant to enzymatic oxidation, and penetrates into the cell through an active transport mechanism using glucose transporters and is more easily absorbed in the intestine since more water-soluble.

Therefore, the invention further relates to PGA in association with Curcumin, for use in the treatment of inflammatory diseases, preferably chronic systemic inflammatory diseases, of humans and animals, resulting from dysfunctions of epithelia and/or synovial membranes.

Therefore, the invention also relates to PGA in association with Polydatin, for use in the treatment of inflammatory diseases, preferably chronic systemic inflammatory diseases, of humans and animals, resulting from dysfunctions of epithelia and/or synovial membranes.

In certain embodiments, PGA and Curcumin and/or Polydatin are intimately mixed to form a dry mixture, for example by means of a powder mixer or similar equipment.

PGA and Curcumin (hereafter referred to as CUR) are used in a weight ratio PGA/CUR from 3:1 to 1:3, preferably from 2:1 to 1:1.

PGA and Polydatin (hereafter referred to as POL) are used in a weight ratio PGA/POL from 20:1 to 5:1, preferably from 12:1 to 8:1.

In a preferred embodiment, the invention relates to PGA, preferably PGA comprising from 3% to 20% by weight of a fatty acid, in a co-micronized form with Curcumin.

In a further preferred embodiment, the invention relates to PGA, preferably PGA comprising from 3% to 20% by weight of a fatty acid, in a co-micronized form with Polydatin.

In one embodiment, the co-micronized mixture PGA/CUR and the co-micronized mixture PGA/POL have a particle size distribution as defined above, measured with a Malvern Mastersizer 3000 tool with Mie calculation algorithm, where at least 96% by volume of particles has a particle size from 0.6 to 10 microns.

Figure 2:
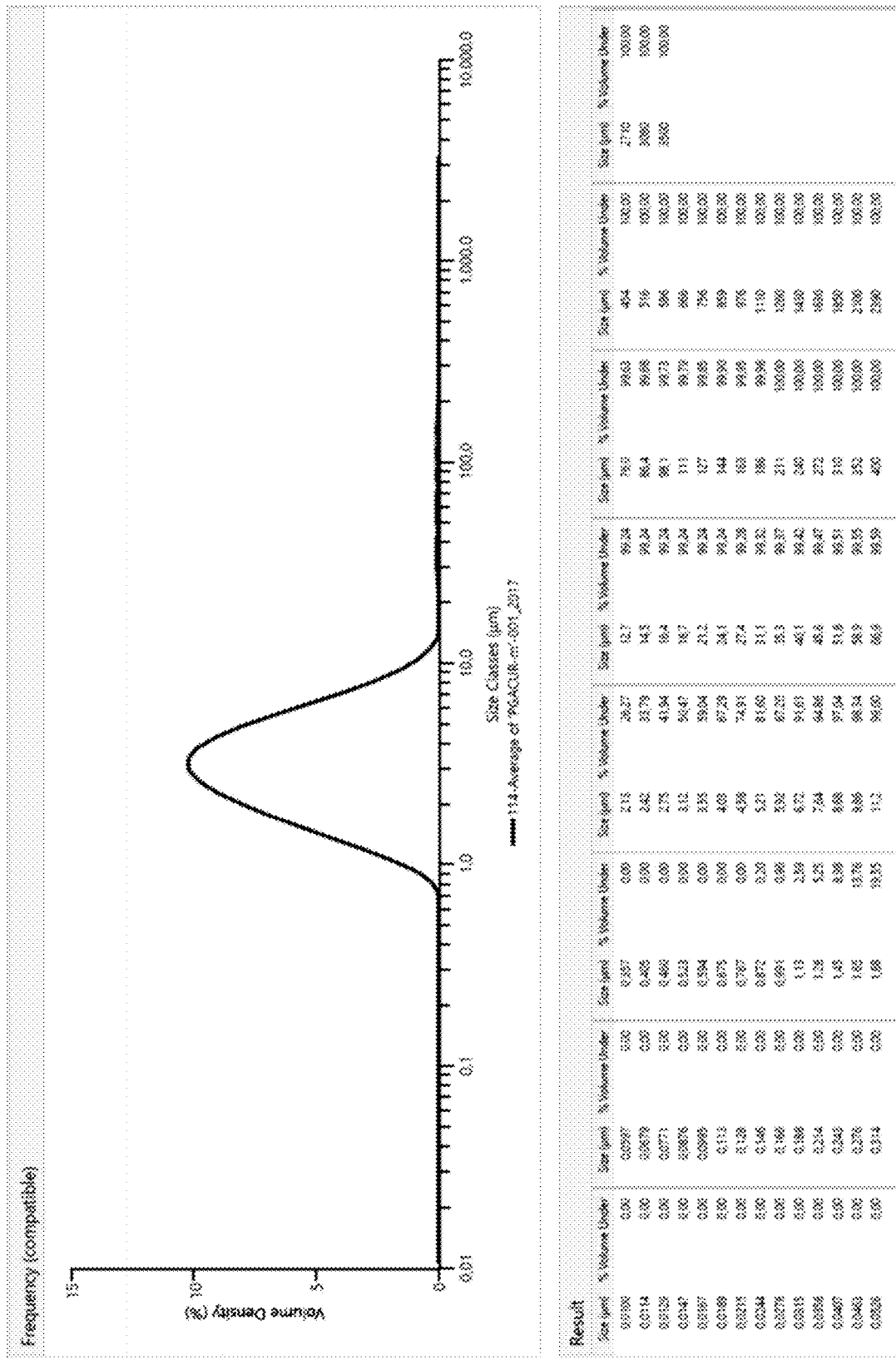
FIG. 2 shows a particle size distribution curve V %/size of N-palmitoyl-D-glucosamine co-micronized with Curcumin.

In a preferred embodiment, the co-micronized mixture PGA/CUR and the co-micronized mixture PGA/POL have a particle size distribution as defined above, measured with a Malvern Mastersizer 3000 tool with Mie calculation algorithm having a mode from 3.1 to 3.8 microns, and having at least 98% by volume of particles smaller than 10 microns, and preferably at least 50% by volume of particles smaller than 3.5 microns. An example of this particle size distribution for the mixture PGA/CUR is shown in the graph and in the attached table in FIG. 2.

PGA in a sub-micron form was also prepared. The term "PGA in a sub-micron form" refers to PGA having a particle size distribution, measured by the laser light scattering method and defined as a percentage by volume of the particles/dimension, represented by a distribution curve with a mode below 300 nanometers.

In this embodiment, PGA has a particle size distribution as defined above, measured with a Malvern Mastersizer 3000 tool with Mie calculation algorithm, where at least 98% by volume of particles has a particle size from 0.06 to 1 micron.

Figure 5:
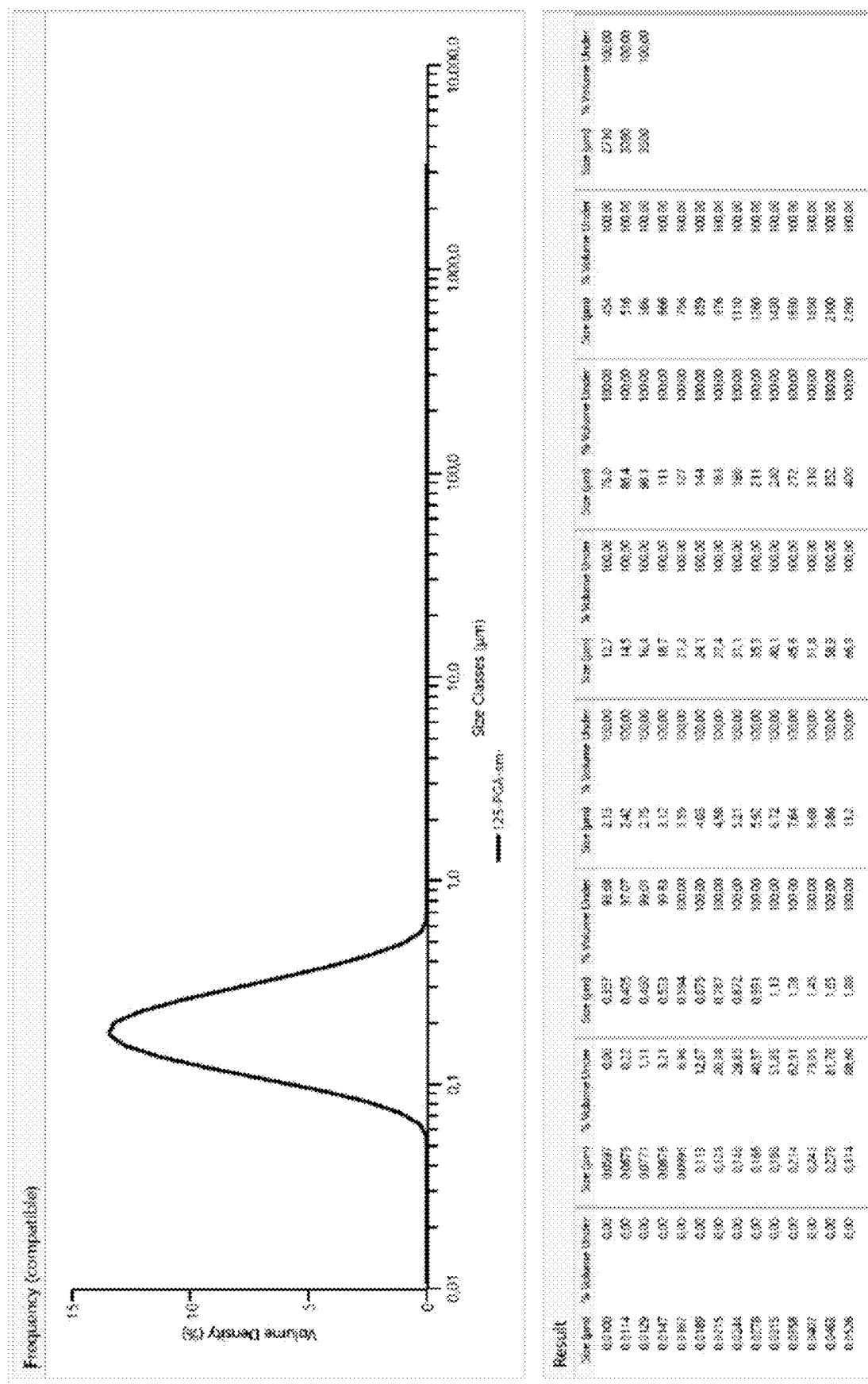
FIG. 5 shows a particle size distribution curve V %/size of N-palmitoyl-D-glucosamine in a sub-micron micronized form.

An example of this particle size distribution is shown in the graph and in the attached table in FIG. 5.

Figure 4:
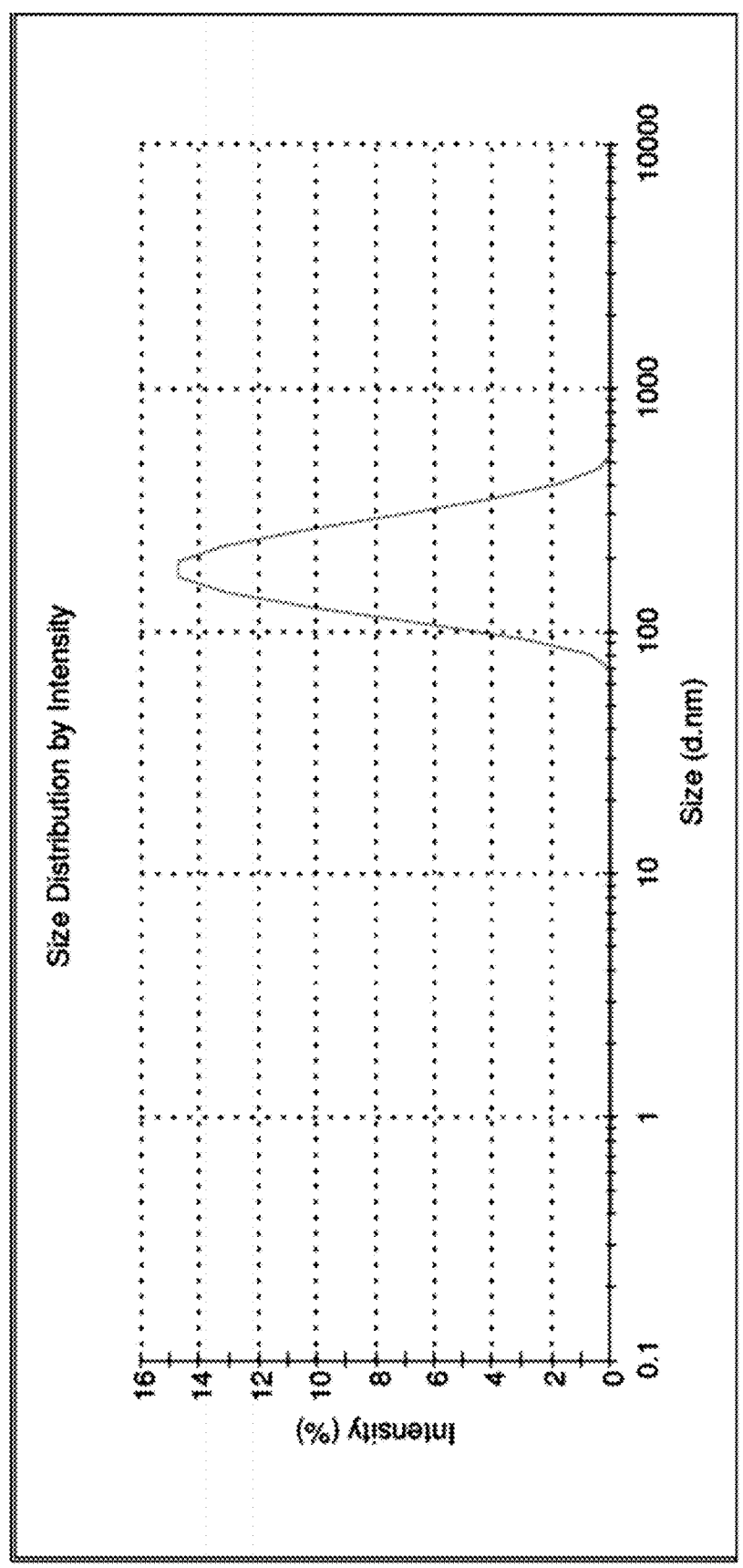
FIG. 4 shows a particle size distribution curve I %/size of N-palmitoyl-D-glucosamine in a sub-micron micronized form.

As a further control, the particle size distribution of PGA in a sub-micron form was also measured using a different instrument, Malvern Nanosizer, specifically used for the study of the particle size in the nanometer range. FIG. 4 shows the relative distribution graph expressed as percentage intensity of diffused light/dimension, using the Mie calculation algorithm. From the graph it can be seen that the obtainable mode is from 170 to 220 nm, which substantially confirms the same particle size distribution as determined by the graph in FIG. 5.

The sub-micron PGA was obtained by a sub-micronization process with the wet milling technique using a microsphere mill as described in the following experimental part. Even in this case, PGA in a sub-micron form was obtained after adding a fatty acid, preferably palmitic acid, as previously described, using 2-20% by weight, preferably 4-10% by weight, of the fatty acid.

The sub-micron PGA surprisingly did not demonstrate, as was indeed predictable, an improved activity compared to the micronized PGA as previously described: on the contrary, it has instead shown a markedly pejorative activity compared to the micronized PGA with the same dose administered.

EXPERIMENTAL

Preparation of High Purity
N-palmitoyl-D-glucosamine (HPPGA 794.3 g of glucosamine hydrochloride (3.68 moles) are solubilized in 6700 ml of water under stirring.

The solution is cooled to −5° C. and 2104 g of sodium carbonate decahydrate (7.36 moles) are added.

1114 g of palmitoyl chloride (4.05 moles), equal to 1228 ml, solubilized in 3000 ml of tetrahydrofuran, are added to the glucosamine solution, slowly over an hour, under very vigorous stirring. The mixture is kept under vigorous stirring for 2 hours at −5° C., then for further 2 hours at room temperature. 17500 ml of water are added, and the mixture is kept under mild stirring overnight.

The formed precipitate is recovered by filtration and washed three times with 3000 ml of water. Mother liquors and washing waters are discarded.

The solid is crystallized from 5000 ml of methanol, keeping it refluxing under continuous stirring for 2 hours, then separated by hot filtration, washed twice with 2000 ml of hot methanol and finally dried under high vacuum.

Approximately 1200 g of dry product are recovered.

The thus obtained N-Palmitoyl-D-Glucosamine product has the following characteristics:
physical state: white powder
molecular formula: $C_{22}H_{43}NO_6$
molecular weight: 417.6
elemental analysis: C=63.28% H=10.38% N=3.35% O=22.99%
melting point: 202° C. (dec.)
TLC, eluent chloroform/methanol/water/$NH_3$ (28%) 80:25:2:1 Rf=0.30
TLC purity: >98%

Preparation of N-palmitoyl-D-glucosamine Added with sodium palmitate (PGA)

950 g of high purity N-palmitoyl-D-glucosamine (HPPGA) are added with 50 g of palmitic acid sodium salt (5% by weight on the total weight of the mixture). The mixture is suspended in 4 liters of methanol under efficient stirring and refluxed for 2 hours. Operating the stirring, the mixture is then progressively cooled to 5° C. within one hour. The solid is then separated by filtration and dried under high vacuum.

The palmitic acid content is controlled by HPLC analysis against an authentic palmitic acid standard:
Column ZORBAX SB-C18 4.6 150 mm 5 micron or equivalent;
Mobile phase: A (0.01 M ammonia buffer—methanol 2 to 1; B acetonitrile. Time 0 min.: A 30% B 70%; Time 25 min. To 10% B 90%; Equilibrium time: 5 minutes;
Flow: 1.0 ml/min;
Column thermostatation: 40° C.;
Analysis time: 25 min;
Injection volume: 50 µl;
Detector: Evaporative Light Scattering Detector: temperature 40° C., gas flow 1.5 ml/min, Gain 4.

Micronization Process

PGA was micronized as an intimate PGA/fatty acid mixture as described above.

Figure 3:
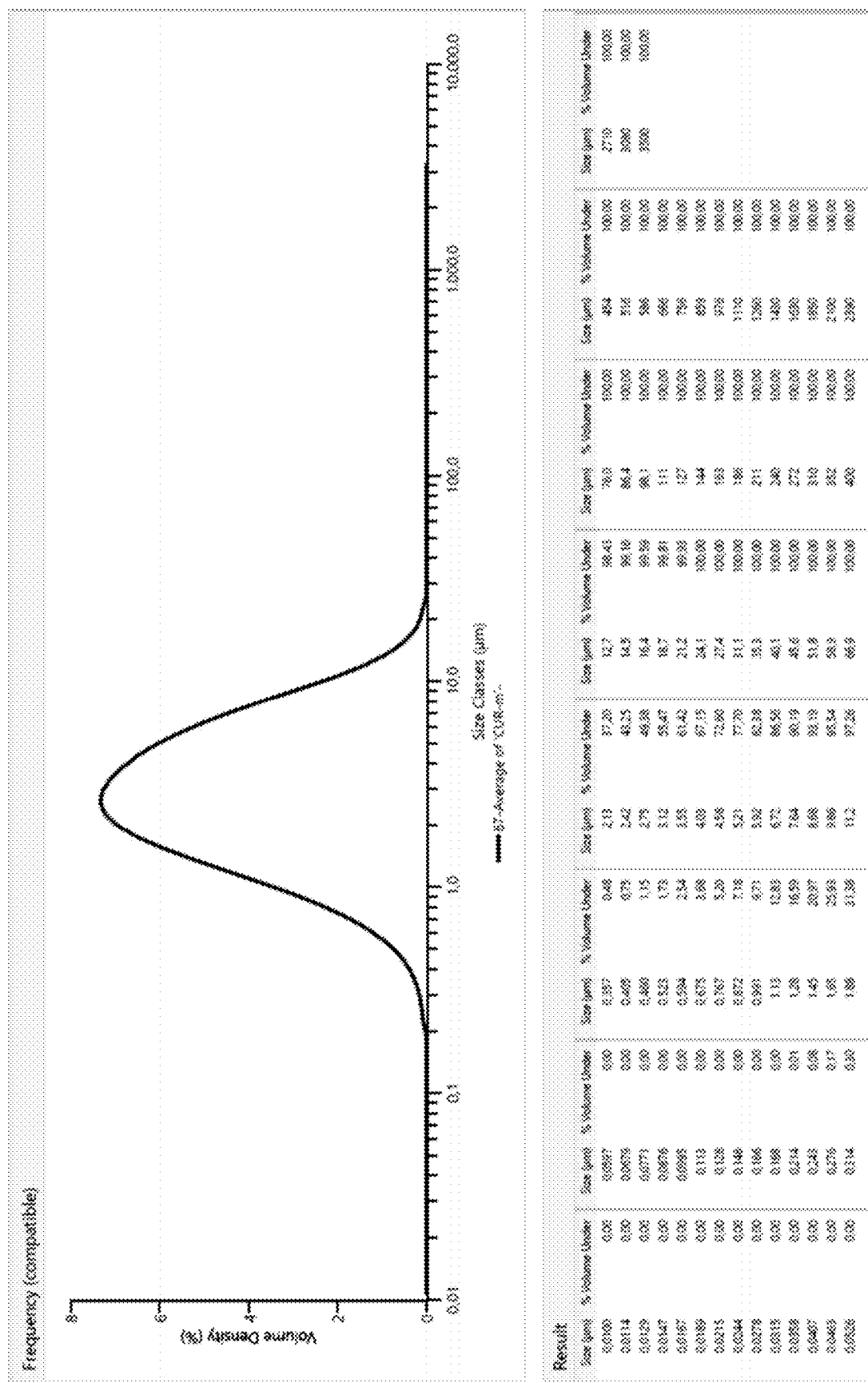
FIG. 3 shows a particle size distribution curve V %/size of micronized Curcumin.

Micronized Curcumin was also prepared as a comparison compound for subsequent biological experiments. Commercial Curcumin with a titer of at least 90% in curcuminoids was used. The particle size distribution of the micronized Curcumin thus obtained is shown in FIG. 3.

Micronization and co-micronization were carried out in all cases in a fluid jet system (in particular, a Jetmill® model) operating with a compressed air jet "spiral technology".

Micronization conditions:
micronization chamber internal diameter 300 mm;
fluid jet pressure 8 bar;
product feeding 20-25 kg/h.

Sub-Micronization Process

The sub-micronization process of PGA (added with fatty acid) was carried out with the "wet milling" technique using a DYNO-MILL MULTILAB WA BACHOFEN-Muttenz Switzerland microspheres mill; Beads 1259.7 g Zirconia 0.3 mm diameter.

50 g of the product are suspended in 1000 ml of distilled water and ground for 4 hours at 40° C. The obtained suspension is discharged and dried by freeze-drying.

Determination of the Particle Size Distribution

The determination of the particle size distribution was carried out on a wet sample, after 1-minute sonication.

A Malvern Mastersizer 3000 tool was used with LALLS (Low Angle Laser Light Scattering) technique and a Mie calculation algorithm. For the determination of the particle size distribution of PGA in a sub-micron form, the Malvern Nanosizer tool was also used as a comparison.

The graphs of particle size distribution are shown in the FIGS. 1-6.

Biological Experimentation

Pharmacological Effects of N-palmitoyl-D-glucosamine (PGA) in Different Physical Forms on Epithelial Dysfunction-Dependent Inflammation The experimental model of carrageenan edema was used in the rat's paw, which determines epithelial dysfunction at the paw level.

The experimental model of carrageenan edema in the paw was induced by sub-plantar injection of a carrageenan solution (containing 50 µl of sterile saline containing 1% carrageenan) into the right paw of the animal (rat).

At specific time intervals the plantar volume was measured by a plethysmometer (Ugo Basile, Milan, Italy). The increase in plantar volume was evaluated as the difference between the value obtained in the specific time intervals and the volume at baseline (time 0) measured immediately before the administration of carrageenan.

The following physical forms of N-palmitoyl-D-glucosamine were tested:
Non-micronized N-palmitoyl-D-glucosamine (PGA);
Micronized N-palmitoyl-D-glucosamine (PGA-m);
N-palmitoyl-D-glucosamine co-micronized with Curcumin (PGACUR-m);
N-palmitoyl-D-glucosamine in a sub-micron form (PGA-sm).

The following physical form of Curcumin was also tested:
Micronized Curcumin (CUR-m)

In all cases PGA was tested as a PGA/fatty acid mixture.

The rats (10 animals per group) were divided into the experimental groups indicated in Table 1.

The thus obtained results, expressed as a percentage of the edema produced only by carrageenan (indicated with a value of 100), are as follows:

TABLE 1

|  | 30 min | 1 hr | 2 hr | 3 hr | 4 hr | 5 hr |
| --- | --- | --- | --- | --- | --- | --- |
| Carrageenan (CAR) + CMC2% | 100.0 | 100.0 | 100.0 | 100.0 | 100.0 | 100.0 |
| CAR + PGA (30 mg/kg) | 100.0 | 100.0 | 100.0 | 100.0 | 100.0 | 100.0 |
| CAR + PGA-m (20 mg/kg) | 100.0 | 92.2 | 80.1 | 71.5 | 70.4 | 75.5 |
| CAR + CUR-m (10 mg/kg) | 100.3 | 95.4 | 95.1 | 94.8 | 96.2 | 97.4 |
| CAR + PGACUR-m (30 mg/kg) | 100.0 | 74.4 | 60.1 | 48.4 | 40.0 | 48.5 |
| CAR + PGA-sm (20 mg/kg) | 100.0 | 100.0 | 98.0 | 97.0 | 98.0 | 98.0 |

Data show a total inactivity of the non-micronized PGA and an almost total inactivity of both the sub-micronized PGA and the micronized Curcumin.

The micronized PGA shows a 24.5% reduction of the Carrageenan edema, while PGA co-micronized with Curcumin highlights, at a dose of the two active ingredients equal to that used for single tests (PGA-m 20 mg/Kg; CUR 10 mg/kg), an edema reduction of 51.5%.

Therefore, an apparent synergistic effect was demonstrated due to the association of the two active ingredients. In fact:

treatment with PGA (non-micronized) at a dose of 30 mg/kg produces no pharmacological effect;
treatment with PGA-m at a dose of 20 mg/kg produces an apparent pharmacological effect;
treatment with PGA-sm at a dose of 20 mg/kg produces no significant pharmacological effect;
treatment with micronized CUR alone, at a dose of 10 mg/kg, produces no significant pharmacological effect;
treatment with PGACUR-m at a dose of 30 mg/kg (corresponding to 20 mg/kg of PGA-m and 10 mg/kg of CUR-m) produces a significant pharmacological effect which is clearly superior to that obtained with PGA-m alone.

Pharmacological Synergistic Effect of N-palmitoyl-D-glucosamine Co-Micronized with Polydatin in Carrageenan Edema Also in this case, the experimental model of carrageenan edema in the rat's paw was used, which determines epithelial dysfunction at the paw level.

The edema was induced by the sub-plantar injection of 50 μl of an aqueous 1% carrageenan solution. At time intervals (30 min, 1 h, 2 h, 3 h, 4 h, 5 h, 6 h) the volume of the injected paw was evaluated by means of a plethysmometer (Ugo Basile, Milan—Italy). The following physical forms of N-palmitoyl-D-glucosamine with or without Polydatin were tested in groups of 10 animals (Wistar strain weighing between 130 and 160 g) for each group, in the dosages indicated in brackets:

Group A) Carrageenan
Group B) Carrageenan+micronized Palmitoylglucosamine (10 mg/kg)
Group C) Carrageenan+micronized Polydatin (1 mg/kg)
Group D) Carrageenan+Palmitoylglucosamine (10 mg/kg)+Polydatin (1 mg/kg) [mixed]
Group E) Carrageenan+Palmitoylglucosamine and co-micronized Polydatin [10:1] (11 mg/kg)

| | Paw volume | | | | | | |
|---|---|---|---|---|---|---|---|
| | Time from treatment | | | | | | |
| Group | 30 min | 1 h | 2 h | 3 h | 4 h | 5 h | 6 h |
| A) | 0.21 | 0.32 | 0.78 | 1.05 | 1.22 | 1.31 | 1.00 |
| B) | 0.23 | 0.33 | 0.81 | 1.00 | 1.21 | 1.33 | 1.05 |
| C) | 0.21 | 0.32 | 0.69 | 1.03 | 1.19 | 1.28 | 0.95 |
| D) | 0.19 | 0.30 | 0.71 | 1.02 | 1.15 | 1.25 | 0.99 |
| E) | 0.21 | 0.23 | 0.38 | 0.45 | 0.55 | 0.56 | 0.59 |

An apparent synergistic effect is demonstrated when the two substances are administered in a co-micronized form compared to the two substances administered separately or simply mixed.

It is therefore apparent that PGA in a micronized form or in association with Curcumin and/or with Polydatin, in particular in the form co-micronized with Curcumin or Polydatin (but not PGA in the sub-micron form), can be used in the treatment of chronic systemic inflammatory diseases of humans and animals, resulting from dysfunctions of epithelia and synovial membranes, in particular diseases preferably selected from:

inflammatory diseases resulting from dysfunctions of the synovial membranes;
inflammatory diseases resulting from dysfunctions of the intestinal mucous membranes;
inflammatory diseases resulting from dysfunctions of the urothelial mucosa;
inflammatory diseases resulting from dysfunctions of the keratinized epithelia.

PGA in a micronized form or in association with Curcumin and/or with Polydatin, in particular in a co-micronized form with Curcumin or Polydatin, can be included in pharmaceutical or veterinary compositions and can be formulated in dosage forms for oral, buccal, parenteral, rectal or transdermal administration.

For oral administration, the pharmaceutical compositions may be found, for example, in the form of tablets or either hard or soft capsules, prepared in a conventional manner with pharmaceutically acceptable excipients as binding agents (e.g. pregelatinized corn starch, polyvinylpyrrolidone or hydroxypropyl methylcellulose); filling agents (e.g. lactose, microcrystalline cellulose, or calcium hydrogen phosphate); lubricants (e.g. magnesium stearate, talc, or silica); disintegrants (e.g. potato starch, or glycolate sodium starch); or inhibiting agents (e.g. sodium lauryl sulfate). Tablets can be coated by methods well known in the art. Liquid preparations for oral administration may be present, for example, in the form of solutions, syrups, or suspensions or may be presented as freeze-dried products to be reconstituted, before use, with water or other suitable vehicles. Such liquid preparations can be prepared by conventional methods with pharmaceutically acceptable additives such as suspending agents (e.g. sorbitol syrup, cellulose derivatives, or edible hydrogenated fats); emulsifying agents (e.g. lecithin or acacia); non-aqueous vehicles (e.g. almond oil, oily esters, ethyl alcohol, or fractionated vegetable oils); and preservatives (e.g. methyl- or propyl-p-hydroxybenzoates or sorbic acid). The preparation can also conveniently contain flavors, dyes and sweetening agents.

Preparations for oral administration can be formulated in an appropriate manner to allow a controlled release of the active ingredient.

For buccal administration, the compositions may be in the form of tablets or lozenges formulated in a conventional manner, which are suitable for absorption into the buccal mucosa. Typical buccal formulations are tablets for sublingual administration.

PGA in a micronized form or in association with Curcumin and/or Polydatin, in particular in a co-micronized form with Curcumin or Polydatin, can be formulated for a parenteral administration by injection. Formulations for injections may be presented in the form of a single dose, e.g. in vials, with an added preservative. The compositions may be present in a form such as suspensions, solutions, or emulsions in oily or aqueous vehicles and may contain formulary agents such as suspending agents, stabilizers and/or dispersants. Alternatively, the active ingredient can be found as a powder to be reconstituted, before use, with a suitable vehicle, for example with sterile water.

According to the present invention, PGA in a micronized form or in association with Curcumin and/or with Polydatin, in particular in a co-micronized form with Curcumin or Polydatin, can also be formulated according to rectal compositions such as suppositories or retention enema, for example containing the basic components of common suppositories such as cocoa butter or other glycerides.

In addition to the above-described compositions, PGA in a micronized form or in association with Curcumin and/or Polydatin, in particular in a co-micronized form with Curcumin or Polydatin, can also be formulated as a depot preparation. Such long-acting formulations may be administered by implantation (e.g. subcutaneously, transcutaneously or intramuscularly), or by intramuscular injection. Thus, for example, PGA in a micronized form or in association with Curcumin and/or with Polydatin, in particular in a co-micronized form with Curcumin or Polydatin, can be formulated with appropriate polymeric or hydrophobic materials (e.g. in the form of an emulsion in a suitable oil) or ion exchange resins or as minimally soluble derivatives.

According to the present invention, the dose of PGA in a micronized form or in association with Curcumin and/or Polydatin, in particular in a co-micronized form with Curcumin or Polydatin, suggested for administration to a human (with a body weight of about 70 kg) ranges from 1 mg to 7 g, or from 10 mg to 700 mg of the active ingredient per dose unit. The dose unit can be administered, for example, 1 to 4 times a day. The dose will depend on the route selected for administration. It should be considered that it may be necessary to continuously change the dosage depending on the age and weight of the patient and also on the severity of the clinical condition to be treated. The exact dose and route of administration will ultimately be at the discretion of the attending physician or veterinarian.

The invention further relates to dietetic compositions, food supplements, foods for special medical purposes (FSMP), and cosmetic compositions (e.g. in the form of a cream) comprising PGA in a micronized form or in association with Curcumin and/or Polydatin, in particular in a co-micronized form with Curcumin or Polydatin.

The term "food for special medical purposes" refers to products authorized according to the Directive of the European Commission to Member States n. 1999/21/CE et seq. This term refers to a product "designed to respond to particular nutritional needs of people suffering from a disease, a disorder or a specific pathological condition" in order to cure or to help to treat the specific pathological state, thus assimilating this FSMP product to a drug.

The formulations according to the invention can be prepared according to conventional methods, such as those described in Remington's Pharmaceutical Sciences Handbook, Mack Pub. Co., N.Y., USA, 17th edition, 1985.

The invention will now be further described by means of the following formulation examples.

Formulation Examples

Example 1—Syrup for Oral Use

One 100 ml bottle contains
PGACUR-m 4,000 mg
Carboxymethylcellulose 3000 mg
Noveon AA1 150 mg
Sweetener 10 mg
Distilled water q.s. to 100 ml.

Example 2—Granules for Veterinary Use 100 g of granules contain:
PGACUR-m 6000 mg
Sorbitol powder 400 mg
Saccharose Palmitate 20 mg
Ingredient attractive for animals mg 30.

Example 3—Tablets for Oral Use for Human or Veterinary Use

One tablet contains:
PGAm 600 mg
Microcrystalline cellulose 200 mg
Croscarmellose sodium 70 mg
Polyvinylpyrrolidone 10 mg
Magnesium stearate 4 mg.

Example 4—Tablets for Oral Use for Human or Veterinary Use

One tablet contains:
PGACUR-m 600 mg
Microcrystalline cellulose 200 mg
Croscarmellose sodium 70 mg
Polyvinylpyrrolidone 10 mg
Magnesium stearate 4 mg.

Example 5—Tablets for Oral Use for Human or Veterinary Use

One tablet contains:
PGACUR-m 300 mg
Microcrystalline cellulose 180 mg
Croscarmellose sodium 60 mg
Polyvinylpyrrolidone 10 mg
Magnesium stearate 4 mg.

Example 6—Hard Gelatin Capsules for Oral Use for Human or Veterinary Use

One capsule contains:
PGACUR-m 400 mg.

Example 7—Soft Gelatin Capsules

One capsule contains:
PGACUR-m 300 mg
Vegetable oil 200 mg
Soy lecithin 50 mg.

Example 8—Soft Gelatin Capsules

One capsule contains:
PGACUR-m 400 mg
Vegetable oil 200 mg
Soy lecithin 50 mg.

Example 9—Suppositories for Rectal Use

PGACUR-m 200 mg
Fat mass for suppositories 1200 mg.

Example 10—Cream for External Local Application on Skin 100 g of cream contain:
PGACUR-m 2000 mg
Demineralized water 71 g
Vaseline oil 10 g
PEG-5 Vegetable sterols 4 g
Sodium pyroglutamate 2 g Stearic acid 2.5 g
Cetostearyl alcohol 2.5 g
Polysorbate 80 2%
Glyceryl monostearate 1.5 g
Silicone oil 1%
Carbomer 0.5%
2-Phenoxyethanol 1%.

Example 11—Tablets for Oral Use for Human or Veterinary Use

One tablet contains:
PGAPOL-m 400 mg
Microcrystalline cellulose 250 mg
Croscarmellose sodium 80 mg
Polyvinylpyrrolidone 15 mg
Magnesium stearate 5 mg.

What we claim is:

1. A human or veterinary composition, comprising N-palmitoyl-D-glucosamine present in a micronized form, and a fatty acid in a percentage by weight from 3% to 20%, with respect to N-palmitoyl-D-glucosamine, wherein said N-palmitoyl-D-glucosamine has a particle size distribution, defined as a percentage by volume and measured by the laser light scattering method, represented by a distribution curve having the mode below 10 micron and above 0.6 micron.

2. The composition according to claim 1, further comprising at least one of Curcumin and Polydatin,
    wherein N-palmitoyl-D-glucosamine, and the least one of Curcumin and Polydatin are in a co-micronized form.

3. The composition according to claim 2, wherein N-palmitoyl-D-glucosamine and Curcumin are in a weight ratio from 3:1 to 1:3.

4. The composition according to claim 2, wherein N-palmitoyl-D-glucosamine and Polydatin are in a weight ratio from 20:1 to 5:1.

5. The composition according to claim 2, wherein the co-micronized N-palmitoyl-D-glucosamine/curcumin mixture has a particle size distribution, measured by a Malvern Mastersizer 3000 tool with Mie calculation algorithm,
    with a particle size distribution curve with a mode between 3.1 and 3.8 microns, and
    with at least 98% by volume of particles smaller than 10 microns.

6. The composition according to claim 2, wherein the co-micronized N-palmitoyl-D-glucosamine/polydatin mixture has a particle size distribution, measured by a Malvern Mastersizer 3000 tool with Mie calculation algorithm,
    with a particle size distribution curve with a mode between 3.1 and 3.8 microns, and
    with at least 98% by volume of particles smaller than 10 microns.

7. The composition according to claim 1, wherein the composition is formulated in dosage forms for oral, buccal, parenteral, rectal or transdermal administration.

8. A dietetic composition, dietary supplement or food for special medical purposes (FSMP), or feed, or nutritional supplements for animals, comprising the N-palmitoyl-D-glucosamine pharmaceutical composition according to claim 1.

9. A cosmetic composition comprising the N-palmitoyl-D-glucosamine composition according to claim 1.

10. The composition according to claim 1, wherein said fatty acid is palmitic acid.

11. The composition according to claim 2, wherein the co-micronized N-palmitoyl-D-glucosamine/curcumin mixture has at least 50% by volume of particles smaller than 3.5 microns.

12. The composition according to claim 2, wherein the co-micronized N-palmitoyl-D-glucosamine/polydatin mixture has at least 50% by volume of particles smaller than 3.5 microns.

13. The composition according to claim 1, wherein the N-palmitoyl-D-glucosamine has a particle size distribution curve having at least 50% by volume of particles smaller than 3.5 microns.

* * * * *